(12) United States Patent
Kressner

(10) Patent No.: US 8,701,235 B2
(45) Date of Patent: Apr. 22, 2014

(54) ELECTRIC TOOTHBRUSH

(75) Inventor: Gerhard Kressner, Altenstadt (DE)

(73) Assignee: Braun GmbH, Kronberg (DE)

( * ) Notice: Subject to any disclaimer, the term of this patent is extended or adjusted under 35 U.S.C. 154(b) by 312 days.

(21) Appl. No.: 13/181,770

(22) Filed: Jul. 13, 2011

(65) Prior Publication Data

US 2012/0011667 A1 Jan. 19, 2012

(30) Foreign Application Priority Data

Jul. 17, 2010 (EP) ..................................... 10007421

(51) Int. Cl.
*A61C 17/34* (2006.01)
(52) U.S. Cl.
USPC ............................... 15/22.4; 15/22.1; 15/22.2
(58) Field of Classification Search
USPC ................................... 15/22.4, 22.1, 22.2, 29
See application file for complete search history.

(56) References Cited

U.S. PATENT DOCUMENTS

2006/0021165 A1 2/2006 Boland et al.

FOREIGN PATENT DOCUMENTS

| DE | 35 44 256 A1 | 6/1987 |
| DE | 41 38 021 | 5/1993 |
| DE | 196 27 752 A1 | 1/1998 |

OTHER PUBLICATIONS

International Search Report for PCT/IB2011/053129 dated Jul. 13, 2011.

*Primary Examiner* — Shay Karls
(74) *Attorney, Agent, or Firm* — John P. Colbert

(57) ABSTRACT

A handle portion of an electric toothbrush includes an electric motor; a first drive shaft being attachable to a head portion axle of a head portion of an electric toothbrush; a second drive shaft being attachable to a housing of a head portion of an electric toothbrush; and a drive comprising a first drive section and a second drive section. The first drive section is located between the electric motor and one of the first drive shaft and the second drive shaft. The first drive section is arranged to convert a rotational motion of the electric motor into an oscillating pivoting of one of the first drive shaft and the second drive shaft. The second drive section is arranged to transfer an oscillating pivoting of the first drive shaft or the second drive shaft to the respective other drive shaft.

9 Claims, 2 Drawing Sheets

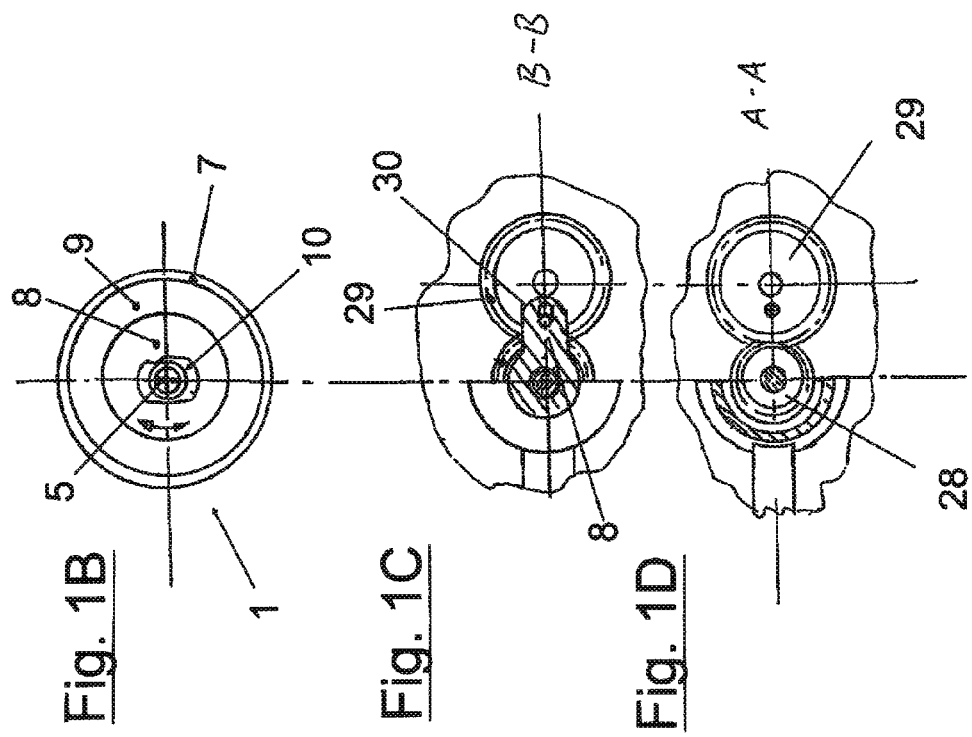
Fig. 1B
Fig. 1C
Fig. 1D
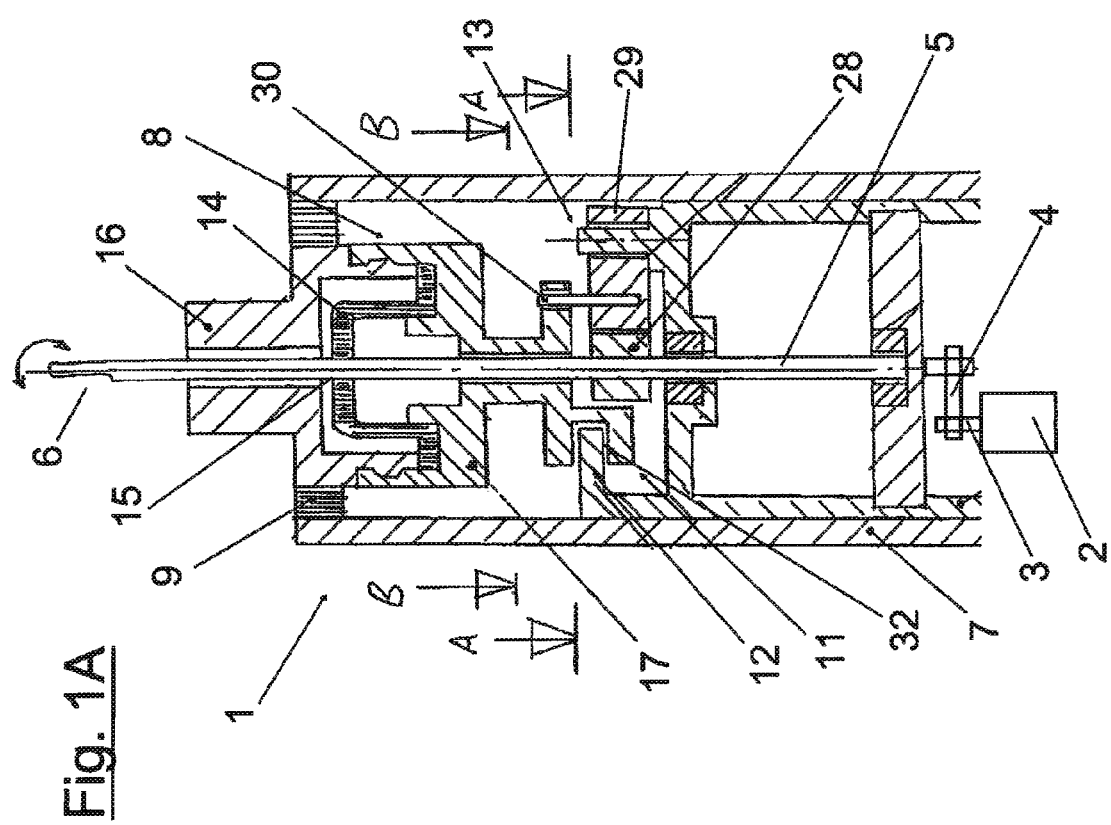
Fig. 1A

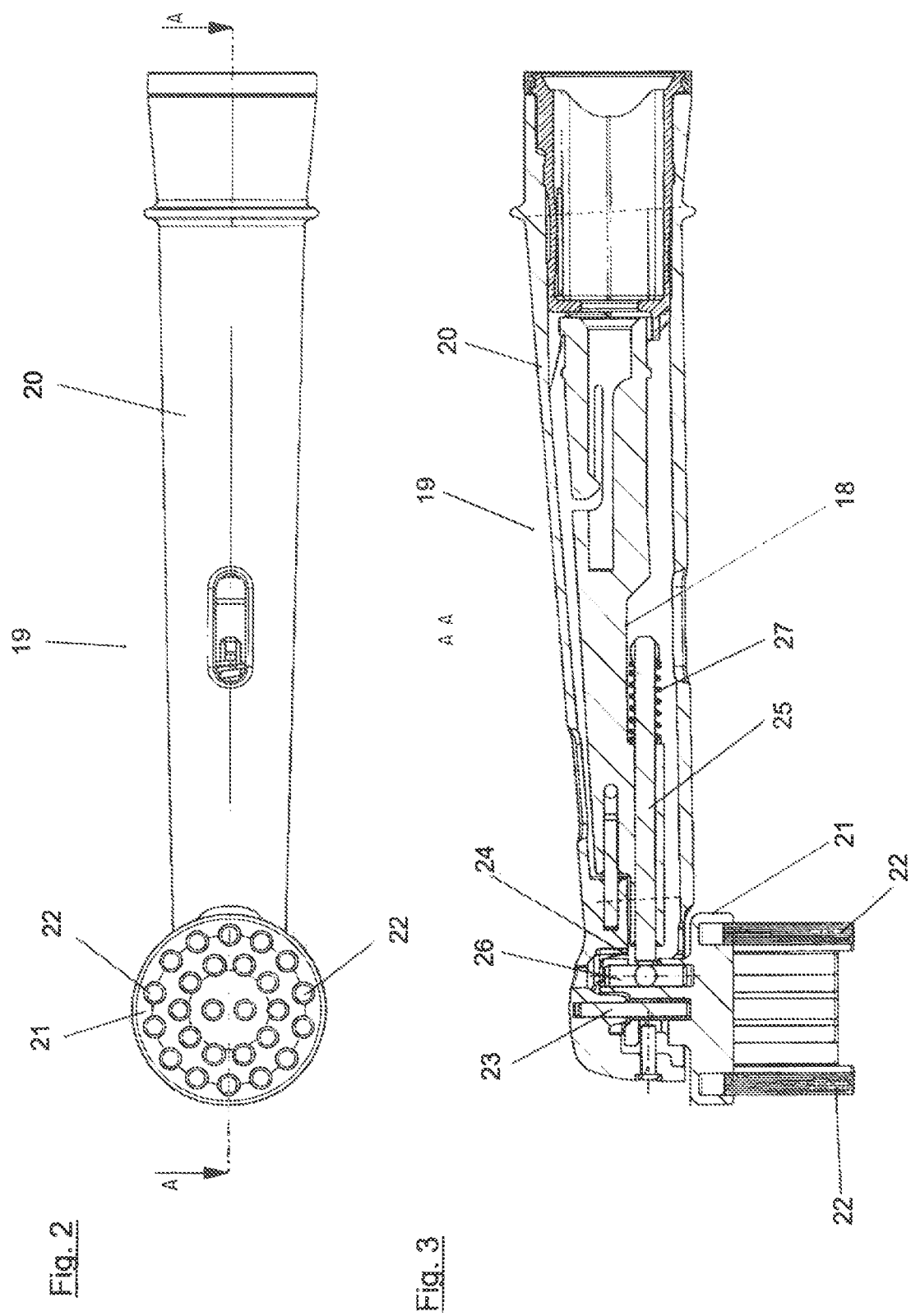

ELECTRIC TOOTHBRUSH

CROSS REFERENCE TO RELATED APPLICATION

This application claims the benefit of European Patent Convention Application No. 10007421.0, filed Jul. 17, 2010, the substance of which is incorporated herein by reference in its entirety.

FIELD OF THE INVENTION

The present disclosure relates generally to the field of electric toothbrushes having a handle portion and a head portion. More particularly, the present disclosure relates to the field of handle portions of electric toothbrushes.

BACKGROUND OF THE INVENTION

Multiple variations of electric toothbrushes are known that include a handle portion and a head portion detachably mounted to each other such that the head portion supporting a bristle carrier having a plurality of bristles may be disposed after extensive use thereof The handle portion provides the majority of mechanical parts and all electric parts of the toothbrush such that the production and cost of the head portion can be kept to a minimum. In order to enable an automatically driven pivoting motion of the bristle carrier and thus the bristles the handle portion includes an electric motor whose rotational motion is converted into an oscillating pivoting via an appropriate drive. This oscillating pivoting motion is provided to a drive shaft which reaches through the housing of the handle portion in order to detachably engage an axle supported by the head portion and thereby enabling a transfer of the pivoting motion of the drive shaft to a head portion axle. The head portion axle in turn is coupled via a head portion drive to the bristle carrier which is rotatably supported by the housing of the head portion and is pivotable around an axis of rotation, which is distinct from the axis of rotation of the head portion axle.

DE 35 44 256 A1 describes an electric toothbrush, wherein the handle portion includes a first and a second drive shaft, each of them being directly coupled to an electric motor. The head portion disclosed includes a first set of bristles mounted to the housing of the head portion and a second set of bristles mounted to the head portion axle. As the head portion axle is coupled to the first drive shaft and the housing of the head portion is coupled to the second drive shaft, the first set of bristles and the second set of bristles do both experience a pivoting motion relatively to each other around an axis of rotation being parallel to the first and second drive shafts of the handle portion. In particular the two sets of bristles do experience a pivoting motion in opposite directions relative to the handle portion. The handle portion according to DE 35 44 256 A1 includes a first drive section being located between the electric motor and the first drive shaft and a second drive section being located between the electric motor and the second drive shaft. Each of the two drive shafts is directly coupled to the electric motor.

In view of the above mentioned there is a desire to provide an electric toothbrush, wherein the bristle carrier provides an oscillating pivoting motion around two distinct axis of rotation being different from each other. It is a further desire to supply a handle portion of an electric toothbrush providing a pivoting of a first and a second drive axis at reduced mechanical effort and reduced cost.

SUMMARY OF THE INVENTION

In one embodiment, an electric tooth brush including a handle portion is disclosed. The electric toothbrush includes a housing, a head portion axle, a bristle carrier and a head portion drive. The handle portion includes an electric motor; a first drive shaft; a second drive shaft; and a drive being arranged to convert a rotational motion of the electric motor into an oscillating pivoting of the first drive shaft and the second drive shaft. The head portion includes a housing being attached to the second drive shaft of the handle portion in order to enable a transfer of an oscillating pivoting of the second drive shaft to an oscillating pivoting of the housing. The oscillating pivoting of the housing occurs around an axis of rotation having a first direction. The head portion axle is attached to the first drive shaft of the handle portion in order to enable a transfer of an oscillating pivoting of the first drive shaft to the head portion axle. The bristle carrier has a plurality of bristles, which is rotatably supported by the housing. The axis of rotation of the bristle carrier has a second direction being different from the first direction. The head portion drive coupling the head portion axle to the bristle carrier in order in order to enable a transfer of an oscillating pivoting of the head portion axle to the bristle carrier.

In another embodiment, a handle portion of an electric toothbrush is disclosed. The handle portion includes an electric motor; a first drive shaft being attachable to a head portion axle of a head portion of an electric toothbrush; a second drive shaft being attachable to a housing of a head portion of an electric toothbrush; and a drive comprising a first drive section and a second drive section. The first drive section is located between the electric motor and one of the first drive shaft and the second drive shaft. The first drive section is arranged to convert a rotational motion of the electric motor into an oscillating pivoting of one of the first drive shaft and the second drive shaft. The second drive section is located between the first drive shaft and the second drive shaft. The second drive section is arranged to transfer an oscillating pivoting of the first drive shaft or the second drive shaft to the respective other drive shaft.

BRIEF DESCRIPTION OF THE DRAWINGS

While the specification concludes with claims which particularly point out and distinctly claim the subject matter that is regarded as the invention, it is believed the various embodiments will be better understood from the following description taken in conjunction with the accompanying drawings, in which:

FIG. 1A shows a cross-sectional side view of a handle portion according to one or more embodiments illustrated and described herein;

FIG. 1B shows a top view onto the handle portion of FIG. 1A;

FIG. 1C shows a cross-sectional view through the handle portion along a line B-B shown in FIG. 1A;

FIG. 1D shows a cross-sectional view through the handle portion along a line A-A shown in FIG. 1A;

FIG. 2 shows a head portion of a toothbrush in a top view onto the bristle carrier according to one or more embodiments illustrated and described herein; and FIG. 3 shows a cross-sectional side view through the head portion according to FIG. 2 along a line A-A.

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to one embodiment, an electric toothbrush includes a handle portion which has an electric motor, a first drive shaft, a second drive shaft, a drive being arranged to convert a rotational motion of the electric motor into an oscillating pivoting of the first drive shaft and of the second drive shaft. In another embodiment, the electric toothbrush may further include a head portion that comprises a housing being attached to the second drive shaft of the handle portion in order to enable a transfer of an oscillating pivoting of the second drive shaft to an oscillating pivoting of the housing, wherein an oscillating pivoting of the housing occurs around an axis of rotation having a first direction, a head portion axle being attached to the first drive shaft of the handle portion in order to enable a transfer of an oscillating pivoting of the first drive shaft to the head portion axle, a bristle carrier having a plurality of bristles, which is rotatably supported by the housing, wherein the axis of rotation of the bristle carrier has a second direction being different from the first direction, a head portion drive coupling the head portion axle to the bristle carrier in order to enable a transfer of an oscillating pivoting of the head portion axle to the bristle carrier. Here, the term "bristle" stands for any type of cleaning elements, being it bristles formed from filaments, elastomeric cleaning elements etc.

In one embodiment, the bristle carrier and thus the bristles automatically perform two superposed pivoting motions around two distinct axes of rotation when in use. The first pivoting motion is a pivoting motion around an axis of rotation which is essentially parallel to the extension of the head portion and it is driven by a pivoting of the second drive shaft being transferred to the housing of the head portion. The second pivoting motion is a pivoting of the bristle carrier around an axis of rotation being distinct from the axis of rotation of the housing. The second axis of rotation in the second direction may be perpendicular to the axis of rotation in the first direction of the housing of the head portion.

In an embodiment, the head portion drive may be a so called con rod drive, wherein the pivoting motion of the head portion axle is transferred into a pivoting motion of the bristle carrier around an axis of rotation which is essentially perpendicular to the head portion axle by a con rod which is attached to the head portion axle eccentrically from the axis of rotation of the head portion axle and which is attached to the bristle carrier at a point being eccentrically located from the axis of rotation of the bristle carrier. In an alternative embodiment, the head portion drive may be a bevel gear transforming the pivoting motion of the head portion axle into a pivoting motion of the bristle carrier. In an embodiment, the angular range of the pivoting motion of the bristle carrier may be equal to or less than about 70° (i.e. the pivoting motion may cover an angular range of about +/−35° around a position of rest).

In one embodiment, the handle portion includes an electric motor, a first drive shaft being attachable to an axle of a head portion of an electric toothbrush, a second drive shaft being attachable to a housing of a head portion of an electric toothbrush, a drive comprising a first drive section and a second drive section, wherein the first drive section is located between the electric motor and one of the first drive shaft and the second drive shaft, wherein the first drive section is arranged to convert a rotational motion of the electric motor into an oscillating pivoting of one of the first drive shaft and the second drive shaft, and wherein the second drive section is located between the first drive shaft and the second drive shaft, wherein the second drive section is arranged to transfer an oscillating pivoting of the first drive shaft or the second drive shaft to the respective other drive shaft.

According to a handle portion of the present disclosure, a mechanical chain is established from the electric motor via a first drive section to one of the two drive shafts and further via a second drive section to the respective other drive shaft. In one embodiment, the first drive section converts the rotational motion of the electric motor into an oscillating pivoting of one of the two drive shafts, whereas the second drive section transfers the oscillating pivoting of one drive shaft to the other drive shaft. The first drive section may be arranged to include a first gear wheel attached to the drive shaft of the electric motor carrying an eccentric pin which in turn engages into a long hole of a lever being pivotably supported by the housing. The engagement of the eccentric pin into the long hole of the lever leads to an oscillating pivoting of the lever once the drive shaft of the electric motor is rotated in one or the other direction. If then one end of the lever combs with a gear wheel attached to the first drive shaft, the first drive shaft experiences an oscillating pivoting motion corresponding to the pivoting of the lever.

Any other form of conversion of the rotational motion of the electric motor into an oscillating pivoting of the first drive shaft is also suitable for application in an embodiment of the present disclosure.

In an embodiment, the first and the second drive shaft may be at least partly concentrically arranged with respect to each other. In a particular embodiment the first drive shaft may be at least partly surrounded by the second drive shaft readily enabling a coupling of a housing of a head portion of a toothbrush to the second drive shaft of the handle portion and a coupling of the head portion axle which may be located inside the housing of the head portion to the first drive shaft of the handle portion. In an embodiment, the first drive section may be arranged between the electric motor and the first drive shaft and the second drive section may be arranged between the first drive shaft and the second drive shaft. This arrangement allows sticking to the well established arrangement of the electric motor, the first drive shaft for coupling to an axle of a head portion of an electric toothbrush.

In an embodiment, the second drive section may include a first gear wheel mounted to one of the first drive shaft and the second drive shaft, the first gear wheel engaging a second gear wheel pivotably supported by a housing of the handle portion, wherein the second gear wheel eccentrically carries a pin, and wherein the pin engages a lever mounted to one of the second drive shaft and the first drive shaft. This embodiment of the second drive section is suitable for transferring the oscillating pivoting motion of the first drive shaft to the second drive shaft in embodiments in which the first drive shaft is coupled via the first drive section to the electric motor as well as in embodiments in which the oscillating pivoting motion of the second drive shaft has to be transferred to the first drive shaft when the electric motor is coupled via the first drive section to the second drive shaft. Further, the described embodiment of the second drive section allows for a design of the handle being restricted to a minimum number of parts and thus facilitating production and reducing costs.

The design of the second drive section as described before may be used in order to provide the first drive shaft as well as the second drive shaft with an oscillating pivoting in the same direction. In order to achieve a pivoting of the first and second drive shafts in the same direction the pin may be arranged between an axis of rotation of the second gear wheel and an axis of rotation of one of the first drive shaft and the second drive shaft. Alternatively, the above described design of the second drive may be used in order to provide a pivoting motion the first and second drive shafts in opposite directions. In order to do so, in an embodiment, the pin when considered in a side view is arranged relative to the axis of rotation of the second gear wheel on a side of the second gear wheel opposite to the axis of rotation of at least one of the first drive shaft and the second drive shaft.

In an alternative embodiment, the second drive section may include a first gear wheel mounted to one of the first drive shaft and the second drive shaft, and a second gear wheel mounted to the respective other drive shaft, wherein the first and the second gear wheel either both engage a third gear wheel or the first gear wheel engages a third gear wheel and the second gear wheel engages a fourth gear wheel, wherein the third and the fourth gear wheel are mounted on the same axis of rotation in order to transfer a pivoting of one of the drive shafts into a pivoting of the other drive shaft in the same direction. Alternatively, a second drive section only consisting of gear wheels engaging or combing with each other may be designed in order to provide a pivoting motion of the first and second drive shafts in opposite rotational directions. In such an embodiment, the second drive section includes a first gear wheel mounted to one of the first drive shaft and the second drive shaft, and a second gear wheel mounted to the respective other drive shaft, wherein the first gear wheel engages a third gear wheel and the second gear wheel engages a fourth gear wheel, wherein the third gear wheel and the fourth gear wheel do form a reversing gear in order to transfer a pivoting of one of the drive shafts into a pivoting of the other drive shaft in opposite rotational directions.

In one embodiment, the second drive shaft may be pivotably supported at a housing of the handle portion by an elastomeric bearing section. Such an elastomeric bearing section may be arranged between the housing of the handle portion and the second drive shaft, thus not only enabling a pivoting motion of the second drive shaft but also providing a sealing for preventing any (in particular liquid) substances from entering into the housing through the gap formed between the housing and the second drive shaft. In an embodiment, the elastomeric bearing section circularly encloses the second drive shaft.

In one embodiment, the second drive shaft may be supported pivotably at the housing of the handle portion. It may be desirable to provide a fixing of the second drive shaft in a direction essentially parallel to the axis of rotation of the second drive shaft. Therefore, in an embodiment, the second drive shaft may comprise a mounting section, which in a direction parallel to the axis of rotation of the second drive shaft is in form fit engagement with a section of a housing of the handle section in order to prevent a translational motion of the second drive shaft in a direction parallel to the axis of rotation of the second drive shaft.

In an embodiment, the second drive shaft may be formed by an upper part and a lower part being in engagement with each other, wherein the upper part and the lower part do form a hollow space through which the first drive shaft extends, wherein a seal membrane is clamped between the upper part and the lower part, wherein the seal membrane extends across the hollow space dividing the hollow space into an upper section and a lower section, wherein the first drive shaft extends through the seal membrane while the seal membrane is in sealing engagement with the first drive shaft. This embodiment effectively seals the second drive shaft against the first drive shaft preventing any liquid from entering into the handle portion between the first and second drive shafts.

In another embodiment, the pivoting motion of the second drive shaft may cover an angular range that is equal to or less than 45° (i.e. the angular range may be +/−22.5° out of a rest position). This will enable an effective cleaning of the teeth corresponding to the manual motion provided by a user's hand to a toothbrush when cleaning the teeth in a direction parallel to the interdental spaces, i.e. for removal of substances out of these interdental spaces.

In a further embodiment the pivoting motion of the first drive shaft may cover an angular range that is equal or less than 70° (i.e. the angular range may be +/−35° out of a rest position). Depending on the gearing in the head portion this leads also to a pivoting motion of the bristle carrier covering an angular range of 70° or less when in use. In an embodiment, the angular range of the first drive shaft may be reduced when the pivoting motion is transferred to the bristle carrier, i.e. the angular range of the first drive shaft may be 70° while the angular range of the bristle carrier may be 45°.

In an embodiment, the mechanical coupling between the first and the second drive shafts provided by the second drive section may be detachable. This enables to interrupt the pivoting motion of the second drive shaft and therefore the pivoting motion of the housing of the head portion either by the user's decision or automatically for example when certain forces are exceeded in order to prevent damage to the user's teeth.

FIG. 1A shows a cross-sectional side view through a handle portion of an exemplary electric toothbrush. In one embodiment, the handle portion 1 is driven by an electric motor 2 located in the lower section of the handle portion 1. The electric motor 2 includes a drive axle 3 which is rotating during operation. The rotational motion of the drive axle 3 is converted by a first drive section 4 into a pivoting motion of the first drive shaft 5. In FIG. 1 the first drive section 4 is schematically indicated. However, in a particular embodiment the first drive section 4 may be formed by a gear wheel attached to the drive axle 3 of the electric motor 2 including an eccentric pin. The eccentric pin of the gear wheel in turn engages into a long hole of a lever attached to the first drive shaft 5. Each turn of the gear wheel thus provides an oscillating pivoting motion of the lever and thus of the first drive shaft 5. The first drive shaft 5 is a metal axle extending from the first drive section 4 to the upper section of the handle portion 1 such that its upper end 6 reaches through the housing 7 or more specifically through the second drive shaft 8. This way the first drive shaft is accessible from outside of the housing.

The second drive shaft 8 is concentrically surrounding a section of the first drive shaft 5 and terminates the housing 7 of the handle portion 1 at its upper end. The concentric arrangement of the first drive shaft 5 and the second drive shaft 8 can be readily understood from FIG. 1B depicting a top view onto the upper end of the handle portion 1. The first drive shaft 5 forms the center of the concentrically arranged elements. The first drive shaft 5 extends through a bore 10 in the second drive shaft 8. The second drive shaft 8 is formed as a hollow element such that the first drive shaft 5 can reach through the second drive shaft 8. The second drive shaft 8 in turn is surrounded by a ring 9 formed of an elastomeric plastic material extending in a radial direction between the second drive shaft 8 and the housing 7 of the handle portion 1. The elastomeric ring 9 serves as a sealing between the second drive shaft 8 and the housing 7 in order to prevent any liquid from entering into the housing through the gap formed between the second drive shaft 8 and the housing 7. The elastomeric ring 9 may additionally or alternatively also serve as a bearing for the second drive shaft 8, thus allowing a pivoting motion of the second drive shaft 8 around an axis of rotation which is parallel to and identical with the axis of rotation of the first drive shaft 5.

In order to prevent any motion in a direction parallel to its axis of rotation the second drive shaft 8 at its lower end comprises a mounting section 11 formed by a U-shaped recess 32 into which recess a holding projection 12 of the housing 8 engages in a form fit manner. The form fit only applies in a direction parallel to the axis of rotation of the second drive shaft 8 and therefore allows a pivoting of the second drive shaft 8 around its axis of rotation.

The second drive shaft 8 forms a hollow body having a through hole extending through the entire second drive shaft 8 through which the first drive shaft 5 extends. In order to prevent any liquid which may enter through the gap formed between the first drive shaft 5 and the second drive shaft 8 into the hollow body of the second drive shaft 8 from further entering into the lower section of the handle portion 1 in particular into the regions carrying the drive sections 4, 13, the handle portion comprises a sealing membrane 14 which seals the first drive shaft 5 with respect to the second drive shaft 8. The sealing membrane 14 extends across the entire cross-section of the hollow body formed by the second drive shaft 8 leaving only a tiny hole 15 in its center through which the first drive shaft 5 reaches through. The through hole 15 in the sealing membrane 14 is dimensioned such that it flexibly engages the first drive shaft 5 in all modes of operation effectively sealing the upper section of the hollow body formed by the drive shaft 8 with respect to the lower section of this hollow body. The sealing membrane 14 extends radially outwards from the first drive shaft 5 to the second drive shaft 8. In one embodiment, the second drive shaft 8 is a two part element having an upper part 16 and a lower part 17 which are in form fit engagement with each other forming a recess in which the sealing membrane 14 is clamped and held in place.

In one embodiment, the upper end 6 of the first drive shaft 5 is flattened in order to provide a possibility for a form fit engagement with a complementary recess 17 of the head portion axle 18 of a head portion 19 of an electric toothbrush. The second drive axis 8 may at its upper end include a recess for form fit engagement with the housing 20 of a respective head portion of an electric toothbrush. The flattening of the upper end 6 of the first drive shaft 5 and the recess of the upper end of the second drive shaft 8 do enable a transfer of any pivoting motion of the first and second drive shafts 5, 8 to the respective parts 18, 20 of the head portion 19.

FIG. 2 shows a side view of an exemplary head portion 19 of an electric toothbrush. The head portion mainly includes a body or housing 20 and a bristle carrier 21 carrying a plurality of bristles for cleaning a user's teeth. The bristle carrier 21 is pivotably mounted on the housing 20 of the head portion 19. Therefore the bristle carrier 21 is attached to an axle 23 which when the head portion 19 is attached to the handle portion 1 is essentially perpendicular to the axis of rotation of the first and second drive shafts 5, 8 of the handle portion as well as to the handle portion axle 18.

When the head portion 19 is attached to the handle portion 1 any pivoting motion of the first drive shaft 5 is transferred to the head portion axle 18. The head portion axle 18 is pivotably mounted inside the housing 20. In order to transfer a pivoting motion of the head portion axle 18 into a pivoting motion of the bristle carrier 21 in a direction perpendicular to the axis of rotation of the head portion axle 18, the head portion includes a head portion drive 24.

The head portion drive 24 may be a con rod drive. The head portion drive 24 is formed by a con rod 25 eccentrically mounted to the head portion axle 18. In turn the con rod 25 at its upper end is connected to a con rod journal 26 which in turn is eccentrically mounted to the bristle carrier 21. In order to enable an effective transfer of the pivoting oscillation of the head portion axle 18 to a pivoting oscillation of the bristle carrier 21 around an axis of rotation being perpendicular to the axis of rotation of the head portion axle 18 the con rod 25 is rotatably mounted at the head portion axle 18 and the con rod journal 26 is rotatably mounted to the bristle carrier 21. Further the con rod 25 is slideably mounted in a direction parallel to the axis of rotation of the head portion axle 18. This slidable motion is spring biased by a spring 27.

When in operating engagement with each other the second drive shaft 8 of the handle portion 1 transfers a pivoting oscillating motion to the housing 20 of the head portion 19 of the electric toothbrush. Thus the bristle carrier 21 not only experiences a pivoting oscillation around an axis of rotation 23 but also a pivoting around an axis of rotation parallel to the axis of rotation of the second drive shaft 8. This superposition of two pivoting motions in two perpendicular directions closely corresponds to the motion as it should be carried out by a person using a manual non-automatic toothbrush.

Returning to FIGS. 1A to 1D it is now described how the pivoting motion imposed by the electric motor 2 and the first drive section 4 onto the first drive shaft 5 is transferred to the second drive shaft 8. In order to transfer any motion of the first drive shaft 5 to the drive shaft 8 a second drive section 13 mechanically connects the first drive shaft 5 to the second drive shaft 8. A first gear wheel 28 is rigidly attached to the first drive shaft 5. The first gear wheel 28 combs with a second gear wheel 29 which is pivotably supported by the housing 7 of the handle portion 1. Any pivoting motion of the first drive shaft 5 is transferred via the first gear wheel 28 to the second gear wheel 29. The second gear wheel carries an eccentric pin 30 which in turn engages a long hole 31 in the second drive shaft 8. The long hole 31 is located off axis with respect to the axis of rotation of the second drive shaft 8. Thus any pivoting motion of the second gear wheel 29 leads to an oscillating translational motion of the eccentric pin 30 on a curved path. As the pin 30 during its translation takes along the pivotably mounted second drive shaft 8 the second drive shaft 8 in turn is forced into a pivoting oscillation.

The design of the second drive section 13 can be better understood when having a look at the cross-sectional views along lines B-B and A-A of FIG. 1A as depicted in FIGS. 1C and 1D. FIG. 1C shows how the pin 30 is eccentrically mounted on the second gear wheel 29 and engages into the long hole 31 of the second drive shaft 8. In FIG. 1D the combing of the first and second gear wheels 28, 29 is depicted.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric tooth brush comprising:
   a handle portion including
      an electric motor;
      a first drive shaft;
      a second drive shaft; and
      a drive comprising a first drive section and a second drive section; wherein the first drive section is arranged to convert a rotational motion of the electric motor into an oscillating pivoting of the first drive shaft and the second drive shaft;
   a head portion including
      a housing being attached to the second drive shaft of the handle portion in order to enable a transfer of an oscillating pivoting of the second drive shaft to an oscillating pivoting of the housing, wherein the oscillating pivoting of the housing occurs around an axis of rotation having a first direction;
      a head portion axle being attached to the first drive shaft of the handle portion in order to enable a transfer of an oscillating pivoting of the first drive shaft to the head portion axle;
      a bristle carrier having a plurality of bristles, which is rotatably supported by the housing, wherein the axis of rotation of the bristle carrier has a second direction being different from the first direction;
      a head portion drive coupling the head portion axle to the bristle carrier in order in order to enable a transfer of an oscillating pivoting of the head portion axle to the bristle carrier, wherein the head portion drive is a con-rod drive;
   wherein the first direction of the axis of rotation of the housing is perpendicular to the second direction of the axis of rotation of the bristle carrier;
   wherein the second drive section includes a first gear wheel mounted to one of the first drive shaft and the second drive shaft; the first gear wheel engaging a second gear wheel pivotably supported by a housing of the handle portion; wherein the second gear wheel eccentrically carries a pin, and wherein the pin engages a lever mounted to one of the second drive shaft and the first drive shaft; and
   wherein the pin when considered in a side view is arranged between an axis of rotation of the second gear wheel and an axis of rotation of one of the first drive shaft and the second drive shaft in order to transfer a pivoting of one of the drive shafts to a pivoting of the other drive shaft in the same rotational direction.

2. A handle portion of an electric toothbrush comprising:
   an electric motor;
   a first drive shaft being attachable to a head portion axle of a head portion of an electric toothbrush;
   a second drive shaft being attachable to a housing of a head portion of an electric toothbrush; and
   a drive comprising a first drive section and a second drive section;
   wherein the first drive section is located between the electric motor and one of the first drive shaft and the second drive shaft; wherein the first drive section is arranged to convert a rotational motion of the electric motor into an oscillating pivoting of one of the first drive shaft and the second drive shaft; and
   wherein the second drive section is located between the first drive shaft and the second drive shaft; wherein the second drive section is arranged to transfer an oscillating pivoting of the first drive shaft or the second drive shaft to the respective other drive shaft;
   a head portion including
   a housing being attached to the second drive shaft of the handle portion in order to enable a transfer of an oscillating pivoting of the second drive shaft to an oscillating pivoting of the housing, wherein the oscillating pivoting of the housing occurs around an axis of rotation having a first direction;
   a head portion axle being attached to the first drive shaft of the handle portion in order to enable a transfer of an oscillating pivoting of the first drive shaft to the head portion axle;
   a bristle carrier having a plurality of bristles, which is rotatably supported by the housing, wherein the axis of rotation of the bristle carrier has a second direction being different from the first direction; and
   a head portion drive coupling the head portion axle to the bristle carrier in order in order to enable a transfer of an oscillating pivoting of the head portion axle to the bristle carrier, wherein the head portion drive is a con-rod drive;
   wherein the first direction of the axis of rotation of the housing is perpendicular to the second direction of the axis of rotation of the bristle carrier; and
   wherein the second drive section includes a first gear wheel mounted to one of the first drive shaft and the second drive shaft; and a second gear wheel attached to the respective other drive shaft; wherein the first and the second gear wheel either both engage a third gear wheel or the first gear wheel engages a third gear wheel and the second gear wheel engages a fourth gear wheel; wherein the third and the fourth gear wheel are mounted on the same axis of rotation, in order to transfer a pivoting of one of the drive shafts to a pivoting of the other drive shaft in the same rotational direction.

3. The handle portion of an electric toothbrush according to claim 2, wherein the second drive shaft is pivotably supported at a housing of the handle portion by an elastomeric bearing section.

4. The handle portion of an electric toothbrush according to claim 2, wherein the second drive shaft includes a mounting section which in a direction parallel to the axis of rotation of the second drive shaft is in form fit engagement with a section of a housing of the handle section in order to prevent a translational motion of the second drive shaft in a direction parallel to its axis of rotation.

5. The handle portion of an electric toothbrush according to claim 2 further comprising a sealing extending between the first drive shaft and the second drive shaft in order to prevent substances from entering into the spacing between the first drive shaft and the second drive shaft.

6. The handle portion of an electric toothbrush according to claim 5, wherein the second drive shaft is formed by an upper part and a lower part being in engagement with each other; wherein the upper part and the lower part do form a hollow space through which the first drive shaft extends; wherein a seal membrane is clamped between the upper part and the lower part; wherein the seal membrane extends across the hollow space diving the hollow space into an upper section and a lower section; wherein the first drive shaft extends through the seal membrane while the seal membrane is in sealing engagement with the first drive shaft.

7. The handle portion of an electric toothbrush according to claim 2, wherein the pivoting motion of the second drive shaft covers an angular range that is equal to or less than 45°.

8. The handle portion of an electric toothbrush according to claim 2, wherein the pivoting motion of the first drive shaft covers an angular range that is equal to or less than 70°.

9. The handle portion of an electric toothbrush according to claim 2, wherein the mechanical coupling between the first and the second drive shaft provided by the second drive section is detachable.

* * * * *